United States Patent [19]

Holtkamp, Sr.

[11] Patent Number: Plant 6,550

[45] Date of Patent: Jan. 24, 1989

[54] AFRICAN VIOLET PLANT NAMED GISELA

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,388

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Gisela, characterized by its beautiful white flowers with dark pink frilled edges; fully developed flower heads, producing a tight bouquet that is free standing; vigorous growth habit; medium to dark green, slightly serrated leaves; and long lasting, non-dropping flowering habit.

1 Drawing Sheet

The present invention comprises a new and distinct cultivar of African violet plant, botanically known as *Santpaulia ionantha,* and hereinafter referred to by the cultivar name Gisela.

The new cultivar was referred to during the breeding and selection process by the designation I11/16, and is a product of a planned breeding program. The new cultivar was originated from a cross made by applicant in a controlled breeding program in Haffen, Federal Republic of Germany. The female, or seed parent was a cultivar designated F38/6 Blue. The male, or pollen parent was a cultivar designated G24/1 Pink.

Gisela was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Gisela has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Gisela which in combination distinguish this African violet as a new and distinct cultivar:

1. Strong upright flower stems curving slightly toward the center.
2. Violet-shaped, white flowers with dark pink edges, especially on the 2 smaller petals; frilled edges.
3. First flash of flowers appears 9–10 weeks after potting and forms a tight bouquet above the leaves.
4. Profuse flowering.
5. Each plant carries 9–10 upright flower stems of which each carries 8–9 and more flowers.
6. Vigorous grower.
7. Plant saleable 10–11 weeks after potting.
8. Medium to dark green, velvety, round to oval leaves, slightly serrated.

9. Long-lasting, non-dropping single flowers.
10. Seed capsules push slightly through.
11. After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (RHS), except where general colors of ordinary significance are referred to. Color values were taken under natural light conditions at approximately 2:00 p.m. in Nashville, Tenn. Under cooler growing conditions and more intensive lighting, the pink color is more intense.

Botanical classification: *Saintpaulia ionantha,* Ramat., cv. Gisela.

Parentage:

*Male parent.*—G24/1 Pink.

*Female parent.*—F38/6 Blue.

Propagation: The new cultivar holds its distinguishing characteristics through successive propagations by leaf cuttings and by division of shoots.

Plant: From 9 to 11 cm tall when grown in pots, and 23–26 cm in diameter when fully grown. The growth rate is vigorous.

*Leaves.*—Shape: Round to oval, slightly serrated. Diameter: 65–75 mm. Texture: Velvety. Ribs and Veins: Upperside visible, underside well pronounced, light green and shiny. Color (upper side): 136A. Color (under side): 147D. Petioles: Strong, upright, light green, hairy.

*Flowers.*—Buds: Bell-shaped, hairy, 7–8 mm before opening. Sepals: Five (5) in number, green. Calyx: Funnel-shaped. Peduncle: Strong, upright, green, sometimes with light purplish touch, hairy.

*Individual flowers.*—Size: 45 to 50 mm in diameter. Shape: Single violet-shaped with frilled edges. Color (upper side): White; edges are 74C. Color (under side): White; edges are 74C. Borne: Each flower stem carries 8–9 and more flowers on strong, upright, wirelike peduncles that are free standing above the leaves. Flowering habit: Flowers 9–10 weeks after potting.

*Reproductive organs.*—Stamens: Two (2) in number. Anthers: Two, composed of 4 anther cells, seed capsule pushes slightly through. Filaments: 5 mm long, yellowish green. Pollen Color: Yellow 7A. Styles: 8 mm long, pink; base of ovary light green.

*Roots.*—Normally developed, white when young, turning slightly brownish when older.

Disease resistance: Good.

General observations: Gisela is a vigorous grower that has beautiful white flowers with dark pink edges on the 2 smaller petals. The pink color can vary in intensity and width (from 1–3 mm) and can sometimes also be found on the 3 larger petals. All the edges are frilled. The fully developed flower head forms a tight bouquet that is free-standing above the medium to dark green slightly serrated leaves. Approximately 10–11 weeks after potting the plant is saleable. The flowers are long-lasting and non-dropping and the seed capsule pushes slightly through.

I claim:

1. A new and distinct cultivar of African violet named Gisela, as described and illustrated, and particularly characterized by its beautiful white flowers with dark pink frilled edges; fully developed flower heads, producing a tight bouquet that is free standing; vigorous growth habit; medium to dark green, slightly serrated leaves; and long lasting, non-dropping flowering habit.

* * * * *

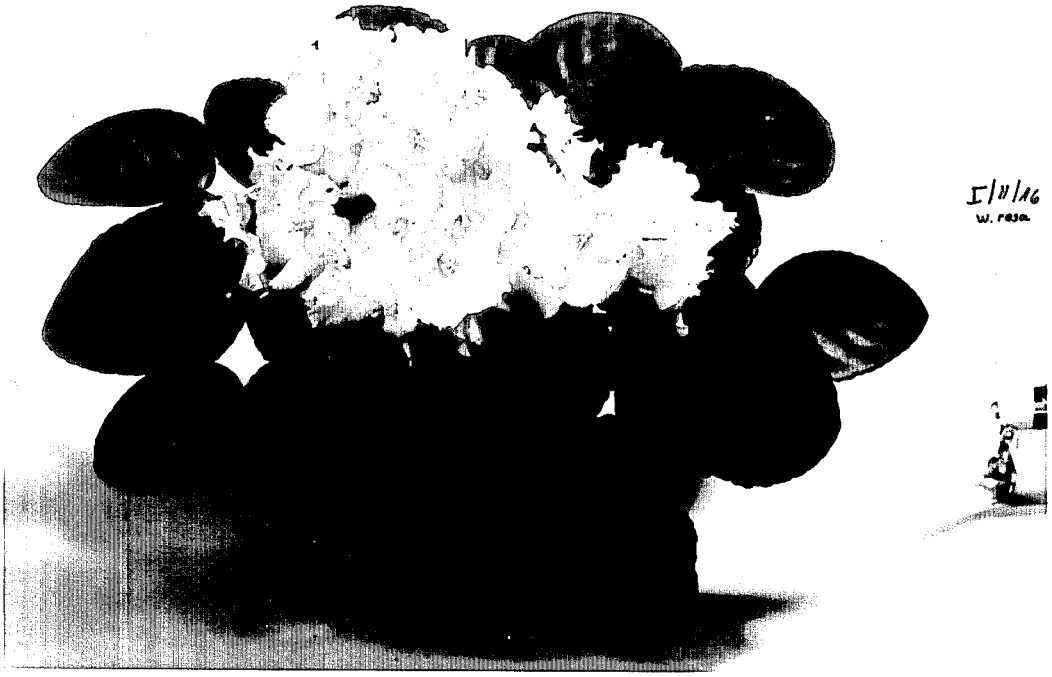
5/11/86
W. Rosa